United States Patent

Shimizu et al.

[11] Patent Number: 5,494,930
[45] Date of Patent: Feb. 27, 1996

[54] CARIBENOLIDE I

[76] Inventors: Yuzuru Shimizu, 188 Linden Dr., Kingston, R.I. 02881; Craig R. Fairchild, 768 Dawes Dr., Yardley, Pa. 19067

[21] Appl. No.: 252,700

[22] Filed: Jun. 2, 1994

[51] Int. Cl.⁶ .................. A61K 31/365; C07D 323/00
[52] U.S. Cl. .................. 514/450; 549/267; 549/268; 549/271
[58] Field of Search ................ 549/267, 268, 549/271; 514/450

[56] References Cited

FOREIGN PATENT DOCUMENTS 2-212490  8/1990  Japan .

*Primary Examiner*—C. Warren Ivy
*Assistant Examiner*—Ba K. Trinh
*Attorney, Agent, or Firm*—Samuels, Gauthier & Stevens

[57] ABSTRACT

Compound (1), isolated from a marine dinoflagellate, is a novel macrolide which has potent in vitro cytotoxicity against human colon carcinoma cell line HCT116 ($IC_{50}$=1.6 nM) and a multiple drug resistant subline. In addition, this compound has good in vivo antitumor activity against a P388 mouse leukemia (150% T/C).

4 Claims, No Drawings

CARIBENOLIDE I

This invention was made with government support under grants U01CA50750/R01CA49992, awarded by the National Institutes of Health, National Institute of Cancer. The government has certain rights in the invention.

FIELD OF THE INVENTION

The invention relates to the biological activity of caribenolide I (1) a pure marine natural product which demonstrates antitumor activity in vivo. This compound has utility for the treatment of human tumors. This novel compound was isolated from a dinoflagellate, *Amphidinium sp.* strain S1-36-5 which was collected from Brewers Beach, St. Thomas, U.S. Virgin Islands.

BACKGROUND AND BRIEF SUMMARY OF THE INVENTION

The present invention relates to a compound which exhibits antitumor activity, a method for isolating the compound from a dinoflagellate and methods for using the compound. More specifically, the present invention relates to the isolation and identification of a new chemical compound and of medically useful compositions containing the same. The compound of the present invention exhibits advantageous pharmacological, toxicological or antitumor properties, such as, for example, killing or inhibiting the growth of human tumors, specifically against a human colon carcinoma cell line HCT 116 (IC50=1.6 nM).

The present invention also is directed to a method of isolating and purifying the compound of the present invention from a dinoflagellate.

Another aspect of the present invention is directed to antitumor compositions which comprise an antitumor effective amount of the compound of the present invention and a pharmaceutically acceptable carrier.

Any of the above antitumor compositions can further include an antitumor effective amount of one or more other known antitumor agents.

The present invention also is directed to a method of treating cancer which comprises administering to a patient in need thereof, an antitumor effective amount of the compound of the present invention.

The method of the present invention also comprises coadministering an antitumor effective amount of one or more other known antitumor agents, together with the compound of the present invention.

Further scope of the applicability of the present invention is apparent from the detailed descriptions and drawings provided below. However, it should be understood that the detailed descriptions and specific examples, which indicating preferred embodiments of the invention are given by way of illustration only, since various changes and modifications within the spirit and scope of the invention will become apparent to those skilled in the art from this detailed description.

DESCRIPTION OF THE PREFERRED EMBODIMENT(S)

The present invention specifically relates to a compound caribenolide I (1) which has novel antitumor activity, methods of obtaining the same from Amphidium sp. strain S1-36-5 compositions containing the same, and methods of using the compound or compositions of the same for treating cancer.

A variety of methods can be used for isolation of the compound of the present invention. Most generally the compound is extracted from a fire alga using an organic solvent. The compound can be further purified by chromatography (column or HPLC) and/or by recrystallization. A fresh fire alga can be used as the source, but generally the alga is frozen immediately after harvesting. This alga is then used directly or freeze-dried before the extraction is done. Preferably, the fire alga is amphidium sp. collected near Brewers Beach, St. Thomas, U.S. Virgin Islands. A preferred general method of isolating the compound of the invention is:

a) obtaining a fresh or frozen sample of the fire alga;

b) extracting the compound from the sample with an organic solvent which dissolves the compound, to form an extract;

c) partitioning the extract between a nonpolar organic solvent and an aqueous solvent, to form a partitioned nonpolar organic extract;

d) chromatographing the partitioned nonpolar organic extract on an adsorption, partition or size exclusion matrix to form fractions; and e) isolating the compound from the fraction containing it.

In step b) the organic solvent which dissolves the compound is generally a mixture of a nonpolar organic solvent and a polar organic solvent; the nonpolar organic solvents include $CH_2Cl_2$, $CHCl_3$, toluene and hexane; the polar organic solvents include MeOH, EtOH, isopropyl alcohol and acetone. In step c) the organic nonpolar solvents include $CH_2Cl_2$, hexane, $CCl_4$, $CHCl_3$, and ethyl acetate; and typical aqueous solvents are mixtures of water and methanol. Solvent mixtures that can be used in this partitioning step are: a) $CH_2Cl_2$ vs 19:1 $H_2O$-MeOH, b) hexane vs 9:1 MeOH-$H_2O$, c) $CCl_4$ vs 8:2 MeOH-$H_2O$, d) $CHCl_3$ vs 7:3 MeOH-$H_2O$, and e) EtOAc VS $H_2O$. In step d) the chromatography is column chromatography and the chromatographic matrix can be the adsorption type, or the partition type or the size exclusion type, or a combination of any of these types. Sephadex LH-20 combines all three of these types and is characterized by mild treatment and good recoveries. Sephadex LH-20 is the most preferred chromatographic matrix material. The isolation of step e) is carried out by either simply evaporating the solvent or by recrystallization.

The definitive proofs of the structure of the compound of the present invention can be obtained by a combination of methods including primary spectral analyses (e.g., high-resolution NMR and mass spectrometry, infrared and UV spectroscopy), comparisons of spectral and physicochemical properties with related literature precedents, and by x-ray crystallographic analysis.

It is believed the novel antitumor activity of the compound of the present invention could be demonstrated in the U.S. National Cancer Institute's new human tumor, disease-oriented screen [Boyd, M. R.: in CANCER: Principles and Practice of Oncology, Update Series (DeVita, V. T. Jr., Hellman, S., and Rosenberg, S. A., eds.), Philadelphia: Lippincott, 1989, pp. 1-1; Boys, M. R.: In Current Therapy in Oncology (Niederhuber, J.E., ed.), Philadelphia: B. C. Decker, Inc., 1991, in press, both of which references are hereby incorporated by reference in their entirety], which accurately predicts antitumor activity of chemical compounds against human cancers. This screen measures the ability of the compound to selectively kill or inhibit the growth of diverse human cancers. More specifically, using this screen, it should be able to show that the compound of the present invention is highly active against certain types of human solid tumors (e.g., brain cancer, renal cancer and colon cancer) which are very resistant or completely resistant to existing antitumor drugs; and, it should show that the compound is also active against other human solid tumors and leukemia cancer cells. By these observations, and with other detailed analyses of the characteristic tumor cellular response profile produced by the compound of the present invention, it should be shown that the same compound is a highly novel antitumor agent with an unprecedented structure activity relationship for treatment of human solid tumors.

Compositions of the present invention comprise as the active ingredient, the compound of the present invention and a pharmaceutically acceptable carrier. Suitable carriers for use in the present invention include, but are not limited to, injectable or orally or rectally administrable oils, lipid emulsions, aqueous solutions or suspensions, or, in the case of orally or rectally administrable tablets or capsules, a pharmacologically inert excipient.

The compound and compositions of the present invention can be shown to kill or inhibit the growth of human cancer, both leukemic and solid tumor cancers, more particularly solid tumors, most particularly tumors of the brain, kidney and colon.

The present invention further relates to a method of preventing or treating cancer comprising administering to a patient an "antitumor effective amount" of a composition of the present invention. The composition can be administered, for example, by intravenous injection or infusion. The composition can also be present in unit dosage form, such as, for example, a tablet or capsulate. The "antitumor effective amount" is the dose necessary to achieve an "effective level" in the individual patient. Since the "effective level" is used as the preferred endpoint for dosing, the actual dose and schedule may vary, depending upon interindividual differences in pharmacokinetics, drug distribution and metabolism. The "effective level" may be defined, for example, as the blood or tissue level desired in the patient that corresponds to a concentration of the compound of the present invention which kills or inhibits the growth of human tumors in an assay which can predict clinical antitumor activity of chemical compounds. The "effective level" for compounds of the present invention also may vary when the compositions of the present invention are used in combination with other known antitumor compounds or combinations thereof. One skilled in the art can easily determine the appropriate dose, schedule, and method of administration for the exact formulation of the composition being used, in order to achieve the desired "effective concentration" in the individual patient. One skilled in the art also can readily determine and use an appropriate indicator of the "effective concentration" of the compounds of the present invention by a direct (e.g., analytical chemical analysis) or indirect (e.g., with clinical chemistry indicators) analysis of appropriate patient samples (e.g., blood and/or tissues), or by direct or indirect observations of the shrinkage or inhibition of growth of the individual patient's tumor. There are many references in the art that teach how one works out the protocols of administering anticancer agents to patients, see for example "Cancer Chemotherapy; Principles and Practice" ed. Chabner and Collins, J. B. Lippincott, 1990, especially chapter 2, by J. B. Collins, which is hereby incorporated by reference in its entirety.

The method of treating cancer using the compound of the invention can be made more effective by administering other anticancer compounds along with the compound of the invention. These other anticancer compounds would include all of the known anticancer compounds approved for marketing in the United States and those that will become approved in the future. See for example Table 1 and Table 2 of Boyd, "The Future of Drug Development", J. E. Niederhuber, Ed., Current Therapy in Oncology; Section I, Introduction to Cancer Therapy; Chapter 2, B. C., Decker, Inc., Philadelphia, 1991, which is hereby incorporated by reference in it entirety). More particularly, these other anticancer compounds would include doxorubicin, bleomycin, vincristine, vinblastine, VP-16, VW-26, cisplatin, procarbozine and taxol for solid tumors in general; alkylating agents, such as BCNU, CCNU, methyl-CCNU and DTIC for brain or kidney cancers; and, antimetabolites such as 5-FU and methotrexate for colon cancer.

Isolation of the Compound of the Present Invention

Chemistry

Three batches of freeze-dried cells derived from *Amphidinium sp.* strain S1-36-5 (17.8g, 20.8g and 16.6g) were individually extracted with toluene/methanol 3:1 (1×200 ml and 3×150 ml each) and were partitioned between n-hexane and 90% aq. methanol (150 ml each). The methanol layer was washed with 4× with 100 ml n-hexane. Combined n-hexane layers were re-extracted with 100 ml 90% aq. methanol, and the 90% aq. methanol extract was washed 2×60 ml n-hexane. The 90% aq. methanol extracts of the three batches were combined (ca. 8 g total) and fractionated on a BAKER silica gel column (3.5×33 cm) with dichloromethane/methanol 95:5. The fraction eluting from 150ml to 390ml (940 mg) was further separated on BAKERBOND c18 (2.2×33 cm) with 80% aq. acetonitrile. The material eluting from 30 ml to 75 ml (75 mg) was purified first by reversed phase HPLC [PRP-1 (Hamilton, 21.5×250 mm, eluted with 80% aq. acetonitrile, 5 ml/min; UV der. 210 nm ($T_r$ 15 min)] and subsequently by normal phase HPLC [Econosil CN (Alltech), 10×250 mm, eluted with isooctane/isopropanol 8:1, 3.5 ml/min (for 17 min), then 6.5 ml/min, UV det. 210 2nm ($T_r \approx 26$ rain)] to yield 14.25 mg (0. 003 dry wt. ) pure compound caribenolide I.

Structure Proof of the Compound of the Present Invention

COMPOUND (1):

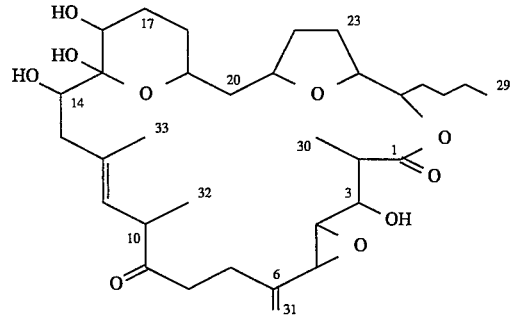

was colorless, amorphous powder (from isooctane/isopropanol, oily from dichloromethane, acetonitrile); UV: no maximum >200 nm (methanol); $[\alpha]D^{25}=+91.4°\pm0.8°$ (c=0.13 in $CH_2Cl_2$), $C_{33}H_{62}O_{11}$, MW 624. 77. NMR data see table 1.

TABLE I

| Pos. | $^{13}C$ | $^1H$ | J [Hz], corr. COSY | |
|---|---|---|---|---|
| 1 | 173.5 s | | | |
| 2 | 46.1 d | 2.62 dq | 8.8 (H3), 7.1 (H30) | |
| 3 | 73.3 d | 3.90 ddd | 8.8 (H2), 4.4 (3OH), 4,4(H4) | |
| | | OH: 4.78 d | 4.4 (H3) | |
| 4 | 62.2 d | 3.04 dd | 4.4 (H3), 2.3 (H5) | |
| 5 | 54.8 d | 3.44 br.d | ~ (H4), (H31b, 7OH)** | |
| 6 | 146.9 s | | | |
| 7 | 70.2 d | 4.54 br.m | 7OH, H8a, H8b, (H31a) | |
| | | OH: 3.56 ?* | H7, (H5)** | |
| 8 | 46.0 t | a: 3.00 dd | 16.5 (H8b), 10.6 (H7) | |
| 9 | 211.1 s | b: 2.54 dd | 16.5 (H8a), 2.4 (H7) | |
| 10 | 48.0 d | 3.40 dq | 10.1 (H11), 6.6 (H32) | |
| 11 | 127.1 d | 4.96 br.d | 10.1 (H10), (H13a, H33) | |
| 12 | 136.9 s | | | |
| 13 | 40.5 t | a: 2.38 br.d | ~13 (H13b), H14, H33, 16OH** | |
| | | b: 2.15 dd | 13.3 (H13a), 11.2 (H14) | |
| 14 | 71.0 d | 4.08 m* | H13a, H13b, 14 OH | |
| | | OH: 3.91 d? | H14, H13a** | |
| 15 | 98.3 s | OH: 3.77 s | | |
| 16 | 66.1 d | 3.55 br.m | 16OH, H17a, H17b | |
| | | OH: 1.83 ?* | H16 | |
| 17 | 27.2 t | a: 2.09 ddd | 13.8, 9.0, 2.7-H17b, H16, H18a,b | |
| | | b: 1.67 ?* | H16, H18a,b*, H17b | |
| 18 | 25.6 t | a: 1.55 ?* | (H18b, H19, H17a, H17b)* | |
| | | b: 1.30 ?* | (H18a, H19, H17a, H17b)* | |
| 19 | 66.5 d | 4.08 m?* | (H18a, H18b)*, H20 | |
| 20 | 41.4 t | 1.64 t (2H) | ~5 (H19, H21)* | |
| 21 | 75.2 d | 4.08 m?* | H20, (H22a,b)* | |
| 22 | 32.9 t | a: 2.00 ?* | H21, (H22b, H23a, H23b)* | |
| | | b: 1.55 ?* | (H21, H22a, H23a, H23b)* | |
| 23 | 28.4 t | a: 2.03 ?* | (H22a, H22b, H24, H23b)* | |
| | | b: 1.55 ?* | (H22a, H22b, H24 H23a)* | |
| 24 | 81.0 d | 3.96 ddd | 8.6 (H25), 6.8, 5.6 - H32a, (H23b)* | |
| 25 | 75.8 d | 4.81 ddd | 8.6 (H24), 7.2, 5.3 (H26ab) | |
| 26 | 30.9 t | 1.49 ?(2H) | H25, (H27)* | |
| 27 | 27.9 t | 1.28 ?(2H) | H26, (H28)* | |
| 28 | 22.9 t | 1.30 ?(2H) | (H27)*, H29 | |
| 29 | 14.1 q | 0.89 br.t (3H) | 6.7 (H28) | |
| 30 | 14.0 q | 1.23 d (3H) | 7.1 (H2) | |
| 31 | 112.7 t | a: 5.18 dd? | 1.1, 1.2 - (H31b, H7) | |
| | | b: 5.11 br.s | (H31a, H5) | |
| 32 | 15.5 q | 1.10 d (3H) | 6.6 (H10) | |
| 33 | 16.1 q | 1.83 s (3H) | (H11, H13a, H13b) | |

*assignments tentative, due to strongly overlapping signals
**possible long - range couplings

In Vitro Cytotoxicity Assay

Cytotoxicity for the pure compound was assessed in several HCT116 cell lines by XTT (2,3-bis(2-methoxy-4-nitro-5-sulfophenyl)-5 -[(phenylamino)carbonyl]-2H-tetrazolium hydroxide assay (Scudiero, 1988). Cells were seeded at 4000 cells/well in 96 well microtiter plates. 24 hrs later drugs were added and serial diluted. The cells were incubated at 37° C. for 72 hrs at which time the tetrazolium dye, XTT, was added. A dehydrogenase enzyme in live cells reduces the XTT to a form that absorbs light at 450 nm and which can be quantitated spectrophotometrically. The greater the absorbance the greater the number of live cells. The results are expressed as an $IC_{50}$ which is the drug concentration required to inhibit cell proliferation (i.e. absorbance at 450 nm) to 50% of that of untreated control cells.

In Vivo Antitumor Activity Determination

For in vivo evaluation of antitumor activity $1 \times 10^6$ P388 mouse leukemia cells were implanted in the intraperitoneal (i.p.) cavity or injected intravenously (i.v.) into (BALB/c ×DBA/2)$F_1$ ($CDF_1$) or (C57/BL6×DBA/2)$F_1$ ($BDF_1$) mice (Roseet al., 1983). Compound (1) was dissolved in DMSO and diluted with saline to the desired concentrations. Injection of Compound (1) was by the i.p. or i.v. route beginning on the first day after tumor implantation and consecutively every day for five treatments (qldX5:1). Increases in lifespan were reflected by the median survival time of treated (T) versus control (C) groups for which a % T/C was calculated. When antitumor activity was evaluated in M109 mouse lung .tumors, 0.2 ml of a 2.0% brei was implanted subcutaneously (s.c.) in $CDF_1$ mice (Rose, 1981). The treatment schedule was one injection per day for days 4–8 after tumor implantation. Results are expressed as % T/C. Tumor growth inhibition was determined by calculating the relative median times for T and C mice to reach a 1 g size. Tumor weights were interchangeable with tumor size on the basis of 1 $mm^3$=1 mg. The activity criterion for tumor growth inhibition (T-C) was approximately equal to a T-C of 4 days. Depending on the tumor volume doubling time for the M109 tumors in control mice, this amount of delay in tumor growth is consistent with about one log of cell kill. For both P388 and M109 tumor models, a T/C of ≦125% was considered an active result.

Results

In Vivo Antitumor Activity

Due to the potent cytotoxicity of Compound (1) in vitro, further evaluation was performed in an in vivo tumor model system. Initial testing was done versus i.p. implanted P388 mouse leukemia. An optimal dose of 0.03 mg/kg/inj given i.p. produced a 50% increase in lifespan (150% T/C). In addition, Compound (1) was evaluated in two distal site models; i.v. implanted P388 or s.c. implanted M109 in which Compound (1) was given by i.v. injection. Compound (1) did not increase the life span of mice bearing i.v. P388 at doses as great as its maximally tolerated dose, 0.064 mg/kg/inj (107%T/C). When Compound (1) was evaluated in s.c. M109, a marginal increase in lifespan (128% T/C) but negligible tumor growth delay (T-C=1.3 days) was observed, which suggests no meaningful distal site activity in this tumor model system.

TABLE II

In Vivo Antitumor Activity of Marine Natural Product Compound (1)

| Tumor[1], site | OD or MTD[2] (mg/kg/inj) | Schedule, route | Maximum Effects | |
|---|---|---|---|---|
| | | | MST[3] % T/C | T-C days |
| P388, ip | a) 0.030 | qd 1-5, ip | 150 | |
| P388, iv | b) 0.064 | qd 1-5, iv | 107 | |
| M109, sc | a) 0.060/0.120 | qd 4-8, iv | 128 | 1.3 |

[1]Murine tumor models used were as follows: P388 leukemia: Madison 109 lung carcinoma.
[2]Shown in either the optimal dose (OD), if the result was one of activity, or the maximum tolerated dose (MTD), or occasionally the highest dose tested, if no activity was observed.
[3]MST % T/C = median survival time of treated vs control mixe, × 100.

Pharmaceutical Compositions

The compound of the present invention or antitumor derivatives thereof may be made into pharmaceutical compositions by combination with appropriate, pharmaceutically acceptable carriers or diluents, and may be formulated into preparations in solid, semi-solid, liquid or gaseous forms such as tablets, capsules, powders, granules, ointments, solutions, suppositories, injections, inhalants, and aerosols in the usual ways for their respective route of administration. In pharmaceutical dosage forms, the compound employed in the present invention maybe used alone or in appropriate association, as well as in combination with other pharmaceutically active compounds, including other antitumor compounds. These other antitumor compounds are described supra.

The following methods and excipients are merely exemplary and are in no way limiting. In the case of oral preparations, the compound of the present invention may be used alone, or in combination with other antitumor agents, together with appropriate additives to make tablets, powders, granules or capsules, e.g., with conventional additives such as lactose, mannitol, corn starch or potato starch; with binders such as crystalline cellulose, cellulose derivatives, acacia, corn starch or gelatines; with disintegrators such as corn starch, potato starch or sodium carboxymethylcellulose; with lubricants such as talc or magnesium stearate; and if desired with diluents, buffering agents moistening agents, preservatives and flavoring agents.

The compound of the present invention may alone, or in combination with other antitumor agents, be formulated into preparation of injections by dissolving, suspending or emulsifying in an aqueous or nonaqueous solvent, such as vegetable oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compound of the present invention, alone or in combination with other antitumor compounds, can be made into aerosol formulations to be administered via inhalation. These aerosol formulations can be placed into pressurized acceptable propellants such as dichlorodifluoromethane, propane, nitrogen and the like.

Furthermore, the compound of the present invention, alone or in combination with other antitumor agents, may be made into suppositories by mixing with a variety of bases such as emulsifying bases or water-soluble bases. The suppository formulations can be administered rectally; the suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, e.g., teaspoonful, tablespoonful, tablet or suppository contains a predetermined amount of the composition containing the compound of the present invention, alone or in combination with other antitumor agents; similarly, unit dosage forms for injection or intravenous administration may comprise a composition as a solution in sterile water, normal saline or other pharmaceutically acceptable carrier.

The term "unit dosage form" as used herein refers to physically discrete units suitable as unitary dosages for human and animal subjects, each unit containing a predetermined quantity of the compound of the present invention, alone or in combination with other antitumor agents, calculated in an amount sufficient to produce the desired effect in association with a pharmaceutically acceptable, diluent, carrier or vehicle. The specification for the novel unit dosage forms of the present invention depend on the particular effect to be achieved, and the particular pharmacodynamics associated with the compound in the individual host.

The pharmaceutically acceptable excipients, for example vehicles, adjuvants, carriers or diluents, are readily available to the public.

One skilled in the art can easily determine the appropriate method of administration for the exact formulation of the composition being used. Any necessary adjustments in dose can be made readily to meet the nature or severity of the cancer, and the individual patient's overall physical health and adjusted accordingly by the skilled practitioner.

The present invention further relates to a method of treating cancer comprising the administration of an "antitumor effective amount" of the composition of the present invention. The "antitumor effective amount" is defined, for example, as that amount required to be administered to an individual patient to achieve an antitumor effective blood and/or tissue level of the compound of the present invention to kill or inhibit the growth of the tumor; the effective blood level might be chosen, for example, as that level to kill or inhibit the growth of tumor cells in a screening assay. Alternatively, the "antitumor effective blood level" might be defined as that concentration of the compound of the present invention needed to inhibit markers of the tumor in the patient's blood, or which slows or stops the growth of the patient's tumor, or which causes the patient's tumor to regress or disappear, or which renders the patient asymptomatic to the particular tumor or which renders an improvement in the patient's subjective sense of condition. Since a fixed "antitumor effective blood level" is used as the preferred endpoint for dosing, the actual dose and schedule for drug administration for each patient may vary depending upon interindividual differences in pharmacokinetics, drug disposition and metabolism. Moreover, the dose may vary when the compound is used in combination with other drug.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described my invention, what I now claim is:

1. A new antitumor compound, in substantially pure form, having the structure:

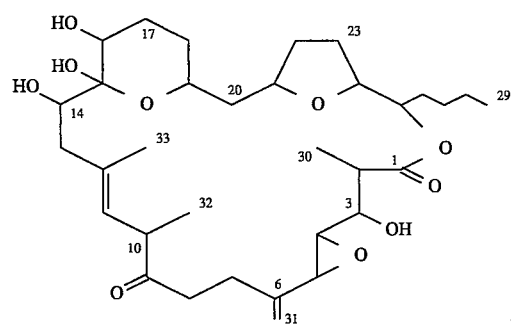

2. A pharmaceutical composition comprising the compound of claim 1 and a pharmaceutically acceptable carrier.

3. A method of treating leukemia or lung cancer which comprises administering to a patient in need thereof, an antitumor effective amount of the compound according to claim 1.

4. The method of claim 3 wherein said compound is administered orally, by inhalation, by injection, as an ointment, or as a suppository.

* * * * *